(12) United States Patent
Evers et al.

(10) Patent No.: US 7,674,929 B2
(45) Date of Patent: Mar. 9, 2010

(54) METHOD FOR THE PRODUCTION OF β-AMINOPROPIONIC ACID DERIVATIVES

(75) Inventors: Holger Evers, Munich (DE); Johann-Peter Melder, Boehl-Iggelheim (DE); Thomas Preiss, Midlevels East-Bamboo Grove (CN); Harald Meissner, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/066,681

(22) PCT Filed: Sep. 13, 2006

(86) PCT No.: PCT/EP2006/066311

§ 371 (c)(1),
(2), (4) Date: Mar. 13, 2008

(87) PCT Pub. No.: WO2007/031534

PCT Pub. Date: Mar. 22, 2007

(65) Prior Publication Data

US 2008/0249333 A1    Oct. 9, 2008

(30) Foreign Application Priority Data

Sep. 15, 2005 (DE) .................. 10 2005 044 090
Feb. 21, 2006 (EP) .................. 06110212

(51) Int. Cl.
*C07C 255/00* (2006.01)

(52) U.S. Cl. ..................................... 558/452

(58) Field of Classification Search ........ None
See application file for complete search history.

(56) References Cited

U.S. PATENT DOCUMENTS

| 3,020,310 A | * | 2/1962 | Fowler et al. .......... 558/455 |
| 4,365,027 A | | 12/1982 | Senyek et al. |
| 4,399,240 A | | 8/1983 | Senyek |
| 5,075,507 A | * | 12/1991 | Carr et al. ............. 564/491 |
| 5,135,970 A | * | 8/1992 | Honel et al. ........... 523/414 |
| 5,434,291 A | | 7/1995 | Witzel et al. |

FOREIGN PATENT DOCUMENTS

| DE | A 58 306 | 10/1967 |
| DE | A 144 765 | 11/1980 |
| DE | 33 34 328 A1 | 4/1985 |
| DE | 222 011 A1 | 5/1985 |
| EP | 0 204 953 A2 | 12/1986 |
| EP | 0 630 886 A1 | 12/1994 |
| GB | 613807 | 12/1948 |

* cited by examiner

*Primary Examiner*—Paul A Zucker
(74) *Attorney, Agent, or Firm*—Oblon, Spivak, McClelland, Maier & Neustadt, L.L.P.

(57) ABSTRACT

The invention relates to a process for preparing β-aminopropionic acid derivatives by reacting a primary or secondary amine with an acrylic acid derivative, wherein comprises (i) a first primary or secondary amine is provided as an amine of value and reacted with the acrylic acid derivative, to obtain a reaction mixture comprising a first β-aminopropionic acid derivative as a product of value and additionally unconverted acrylic acid derivative, (ii) the unconverted acrylic acid derivative present in the reaction mixture is reacted with a second secondary amine as a scavenger amine virtually fully to give a second β-aminopropionic acid derivative to obtain a reaction mixture comprising the first β-aminopropionic acid derivative as a product of value, the second β-aminopropionic acid derivative and unconverted secondary amine.

12 Claims, No Drawings

METHOD FOR THE PRODUCTION OF β-AMINOPROPIONIC ACID DERIVATIVES

The invention relates to a process for preparing β-aminopropionic acid derivatives by reacting a primary or secondary amine with an acrylic acid derivative.

The addition of amines to acrylic acid derivatives such as acrylonitrile is a classic case of addition of nucleophiles to vinylogous carbonyl compounds. The equilibrium between amine and acrylic acid derivative on the one hand and the β-aminopropionic acid derivative on the other lies far over to the product side. Since it is an equilibrium reaction, full conversion of the reactants cannot be achieved at a reactant ratio of 1:1.

Acrylic acid derivatives are toxic, carcinogenic and tend to strongly exothermic polymerization. Crude products with a residual acrylonitrile content of >1000 ppm are classified as toxic. Handling, transport and workup of such mixtures are only permissible with special precautions and in suitable plants. In order to prevent increased concentrations of unconverted acrylic acid derivatives in the crude products, the addition of amine to the acrylic acid derivative is generally carried out with an amine excess. Full conversion of the amine components, which is valuable under some circumstances, is then impossible. Valuable amines which are difficult to remove from the crude product mixture are lost as a result.

DD-A 58 306 discloses a process for preparing 3-dimethylaminopropionitrile, in which 3-dimethylaminopropionitrile is initially charged and saturated with dimethylamine at temperatures of from 10 to 20° C., and the amount of acrylonitrile corresponding to the dimethylamine is subsequently added with cooling at about 20° C. After addition of the acrylonitrile, dimethylamine and acrylonitrile are again added in alternation. From time to time, the reaction product is removed from the reaction vessel and sent to distillation.

DD-A 222 011 discloses a process for continuously preparing 3-N,N-dimethylaminopropionitrile from dimethylamine and acrylonitrile at temperatures between 25 and 100° C., in which dimethylamine is used relative to acrylonitrile in a molar ratio of preferably from 1:1.05 to 1.05:1, the reaction components being used in aqueous or anhydrous form. According to the description, particularly high space-time yields are achieved in the presence of water.

Various techniques are known for removing acrylonitrile from crude products comprising acrylonitrile.

DD-A 144 765 discloses a process for removing the still present acrylonitrile from crude acetonitrile after azeotropic distillation, in which an aliphatic amine, preferably ethanolamine, is added to the crude acetonitrile in amounts of from 0.1 to 5.0% based on the crude acetonitrile. According to the details in the description, especially ethanolamine reacts at from 50 to 90° C. with acrylonitrile to form compounds with a high boiling point which can be removed by distillation to obtain pure acetonitrile.

DE-A 33 34 328 discloses a process for destroying bound hydrocyanic acid and acrylonitrile in crude acetonitrile, in which the crude acetonitrile, if appropriate after distillative removal and recovery of free hydrocyanic acid, is reacted with a base at a pH of from 8.5 to 11, a temperature of from 200 to 250° C. and a residence time of from 3 to 20 minutes. The bases mentioned are alkali metal or alkaline earth metal hydroxides, especially NaOH, which are added in the form of their aqueous solutions.

It is also known that acrylonitrile can be removed from polymer emulsions by reacting with oximes (U.S. Pat. No. 4,365,027), hydroxylamine (EP-A 0 204 953) and heterocyclic amines (U.S. Pat. No. 4,399,240).

The removal of excess acrylonitrile by distillation in industrial vacuum (approx. 20 to 30 mbar) entails high temperatures and long residence times. This forms colored secondary components, whose removal from high-boiling products of value is generally impossible.

When the intention is, for example, to reduce the residual acrylonitrile content by removing acrylonitrile from the crude product of the addition of amine to acrylonitrile under reduced pressure, the temperatures have to remain below 60° C., since formation of colored by-products otherwise distinctly worsens the color number of the product. In order to achieve residual acrylonitrile contents of <1000 ppm under these conditions, very long residence times under reduced pressure are required.

It is an object of the invention to provide a process for preparing β-aminopropionic acid derivatives by reacting a primary or secondary amine as an amine of value with an acrylic acid derivative, in which a crude product which is characterized by very low contents of unconverted acrylic acid derivative is contained. In particular, such a process shall be provided in which the amine of value is largely, preferably substantially fully converted and a crude product which features very low contents of unconverted acrylic acid derivative is nevertheless obtained.

The object is achieved by a process for preparing β-aminopropionic acid derivatives by reacting a primary or secondary amine with an acrylic acid derivative, wherein
(i) a first primary or secondary amine is provided as an amine of value and reacted with the acrylic acid derivative to obtain a reaction mixture comprising a first β-aminopropionic acid derivative as a product of value and additionally unconverted acrylic acid derivative,
(ii) the unconverted acrylic acid derivative present in the reaction mixture is reacted with a second secondary amine as a scavenger amine virtually fully to give a second β-aminopropionic acid derivative, to obtain a reaction mixture comprising the first β-aminopropionic acid derivative as a product of value, the second β-aminopropionic acid derivative and unconverted secondary amine.

In a preferred embodiment of the process according to the invention, the acrylic acid derivative is used in stoichiometric excess with regard to the primary or secondary amino groups of the amine of value which reacts substantially all of the amine of value.

This variant features virtually full conversion of the primary or secondary amine of value to the product of value. Furthermore, since the acrylic acid derivative is used in stoichiometric excess, even comparatively mild reaction conditions are sufficient in order nevertheless to achieve virtually full conversion of the amine of value in acceptable reaction times. Mild reaction conditions suppress the formation of colored by-products.

In a further embodiment, the acrylic acid derivative is used in an essentially equimolar amount with regard to the primary or secondary amino groups of the amine of value. Here too, a very substantial conversion of the amine of value is achieved. In a further embodiment, the acrylic acid is used in a substoichiometric amount with regard to the primary or secondary amino groups.

In each case, reaction with the scavenger amine in step (ii) of the process according to the invention achieves very low residue concentrations of the acrylic acid derivative in the end product without having to use a high excess of the amine of value. Removal of the acrylic acid by distillation, which entails high temperatures and long residence times and thus leads to the formation of coloring secondary components, thus becomes unnecessary.

Examples of amines of value which may be reacted by the process according to the invention are 3,3'-dimethyl-4,4'-diaminodicyclohexylmethane (CAS No. 6864-37-5), 4,4'-diaminodicyclohexylmethane (CAS No. 1761-71-3), 4,4'-diaminodiphenylmethane(CAS No. 101-77-9), hexamethylenediamine (CAS No. 124-09-4), 2-methylpentamethylenediamine (CAS No. 15520-10-2), polyetheramine D 230 (CAS No. 9046-10-0) and 1,13-diamino-4,7,10-trioxamidecane(CAS No. 4246-51-9).

When the acrylic acid derivative is used in stoichiometric excess, it is generally used in an excess of from 0.1 to 10 mol %, preferably from 0.2 to 2 mol %, based on the reacting primary or secondary amino groups of the amine of value, i.e. from 1.001 to 1.10 mol, preferably from 1.002 to 1.02 mol of the acrylic acid derivative are used per mole of primary or secondary amino groups. The amount of acrylic acid derivative used may of course also be higher.

However, it is also possible to use the acrylic acid derivative in stoichiometric deficiency, for example up to 10 mol % (i.e. only 0.9 mol of the acrylic acid derivative is used per mole of reacting amino groups of the amine of the value).

The acrylic acid derivative may be acrylonitrile or an acrylic ester. Typical acrylic esters which may be reacted by the process according to the invention are the $C_1$-$C_6$-alkyl acrylates, preferably methyl acrylate and ethyl acrylate. A preferred acrylic acid derivative is acrylonitrile. Suitable scavenger amines which are reacted in step (ii) with the unconverted acrylic acid derivative present in the reaction mixture are low-boiling or high-boiling secondary amines. Preferred low-boiling secondary amines have a boiling point of up to 100° C. Such low-boiling amines may be removed by distillation directly from the reaction mixture of stage (ii) which comprises the product of value, the further β-aminopropionic acid derivative and unconverted secondary amine. Suitable low-boiling secondary amines are, for example, the di($C_1$-$C_4$-alkyl)amines. A particularly preferred secondary amine used as a scavenger amine is dimethylamine. Further examples are diethylamine, diisopropylamine and dibutylamine. The scavenger amine may be added as a liquid, aqueous solution or else in gaseous form.

Excess scavenger amine may also remain in the reaction mixture. In this case, the scavenger amine will be a relatively high-boiling secondary amine. Examples are N-ethyltoluidine and dicyclohexylamine.

The second β-aminopropionic acid derivative formed by reaction of unconverted acrylic acid derivative and scavenger amine can likewise be removed by distillation from the reaction mixture or remain in the reaction mixture. For many applications of the β-aminopropionic acid derivative obtained as the product of value, the presence of small amounts of the second β-aminopropionic acid derivative formed in step (ii) is not disruptive, so that they can remain in the product mixture without any difficulty. Examples of such applications are the use of the product of value as a hardener for polyurethanes or epoxy resins.

The process according to the invention thus comprises the variants by which, from the reaction mixture obtained in step (ii), (iii) the unconverted secondary amine is removed by distillation, and/or (iv) the second β-aminopropionic acid derivative is removed by distillation, it being possible for no, only one or both of steps (iii) and (iv) to be carried out.

As already mentioned, the reaction of the primary or secondary amine of value with the acrylic acid derivative to give the β-aminopropionic acid derivative can be carried out under mild conditions. For instance, step (i) can be carried out in the presence of water as a catalyst at a reaction temperature of from 20 to 80° C., preferably from 40 to 60° C., acceptable reaction rates and full conversion of the amine of value being achieved even under these mild conditions owing to the acrylic acid derivative excess. Excess acrylic acid derivative and scavenger amine can be reacted in step (ii) of the process according to the invention under the same mild conditions as the main reaction in step (i), no further addition of water being necessary. Selection of a suitable excess of scavenger amine over unconverted acrylic acid derivative makes it possible to ensure that the scavenging reaction in step (ii) is virtually complete. This allows the residual concentration of the acrylic acid derivative to be reduced to concentrations below the limit of detection (approx. 50 ppm). In general, based on unconverted acrylic acid derivative, from 1.5 to 10 times, preferably from 1.5 to 2 times, the amount of scavenger amine (molar ratio), is used.

In the presence of the unconverted excess of the secondary scavenger amine, the storability of the crude product also increases, since the acrylic acid derivatives released by the retro-Michael reaction are scavenged in situ. The risk of coloring or highly exothermic polymerization reactions is greatly reduced by the suppression of free acrylic acid derivatives in the crude product.

Workup of the crude product to isolate the product of value by distillative removal of low boilers (water, unconverted scavenger amine) or of the further β-aminopropionic acid derivative is also possible at relatively high temperatures since no free acrylic acid derivative is present any longer in the crude product mixture.

In a particularly preferred embodiment, the process according to the invention is used in order to react isophoronediamine with two equivalents of acrylonitrile to give N,N-biscyanoethylisophoronediamine. The process can be carried out, for example, as follows:

Isophoronediamine (IPDA) and approx. 10% by weight of water, based on IPDA, are initially charged in a stirred tank and from 2.002 to 2.10 equivalents, for example 2.02 equivalents of acrylonitrile are added dropwise at from 20 to 50° C., for example from 30 to 40° C. Subsequently, the mixture is stirred further at from 50 to 70° C., for example approx. 60° C., for a few hours. Subsequently, from 1.5 to 2 equivalents, based on unconverted acrylonitrile, of dimethylamine (DMA) are added. DMA may be added as an aqueous solution or introduced as a gas. Subsequently, the mixture is stirred further for a few more hours until acrylonitrile has been virtually fully converted. Water and excess DMA are then removed under reduced pressure at from 20 to 30 mbar and from 50 to 60° C. A clear liquid is obtained which comprises <100 ppm of IPDA and <50 ppm of acrylonitrile.

The invention is illustrated in detail by the examples which follow.

EXAMPLES

Example 1

A suitable vessel is initially charged with 1 mol of IPDA and 10% by weight of water based on IPDA. With stirring and temperature control, 2.2 mol of acrylonitrile are metered in at <60° C. After full conversion of the IPDA (>98% biscyanoethyl IPDA), the residual acrylonitrile content is determined by gas chromatography. Subsequently, 2 mol of dimethylamine per mole of residual acrylonitrile are metered in at a temperature of <60° C., and the mixture is stirred until the acrylonitrile has reacted fully (residual acrylonitrile content below the limit of detection). In a suitable apparatus, for example a rotary evaporator, the low boilers (water, dimethylamine and β-diaminopropionitrile) are removed under reduced pressure at approx. 30 mbar. Owing to the mild reaction and workup conditions, a colorless product (color number <10 APHA) is obtained.

Comparative Example 1

Analogously to Example 1, 1.0 mol of IPDA is reacted with 2.2 mol of acrylonitrile under water catalysis. On completion of the reaction, the low boilers (water and acrylonitrile) are drawn off under reduced pressure at approx. 30 mbar. When a residual acrylonitrile content of <1000 ppm is attained, a yellowish product (color number 160 APHA) is present.

Comparative Example 2

Analogously to Example 1, 1.0 mol of IPDA is reacted with only 2.0 mol of acrylonitrile under water catalysis. On completion of the reaction, the residual acrylonitrile content is still >1000 ppm. It is not possible to further lower the residual acrylonitrile content under the mild reaction conditions. After removal of unconverted acrylonitrile under reduced pressure at approx. 30 mbar, a yellowish product (color number 176 APHA) is obtained.

Example 2

The procedure is analogous to Example 1, except that only 2.0 mol of acrylonitrile are reacted with 1 mol of IPDA. After full conversion of the IPDA (>98% biscyanoethyl IPDA), the acrylonitrile content is determined and 2 mol of dimethylamine are added per mole of residual acrylonitrile. Otherwise, the workup is as in Example 1. A colorless product (color number <10 APHA) is obtained.

Example 3

The procedure is as described in Examples 1 and 2, except that only 1.9 mol of acrylonitrile are reacted with 1 mol of IPDA. After conversion of the IPDA to monocyanoethyl IPDA and biscyanoethyl IPDA, the residual acrylonitrile content is determined and 2 mol of dimethylamine are added per mole of residual acrylonitrile. Otherwise, the workup is as in Examples 1 and 2. A colorless product (color number <10 APHA) is obtained.

What is claimed is:

1. A process for preparing β-aminopropionic acid derivatives comprising:
   (i) reacting a primary amine selected from the group consisting of isophoronediamine, 3,3'-dimethyl-4,4'-diaminodicyclo-hexylmethane, 4,4'-diaminodicyclohexylmethane, 4,4'-diaminodiphenylmethane, hexamethylenediamine, 2-methyl-pentamethylene-diamine, polyetheramine D 230 and 1,13-diamino-4,7,10-trioxatridecane, with an acrylic acid derivative to obtain a reaction mixture comprising a first β-aminopropionic acid derivative and unconverted acrylic acid derivative, and
   (ii) reacting the unconverted acrylic acid derivative with a secondary amine to produce a second β-aminopropionic acid derivative and to obtain a reaction mixture comprising the first β-aminopropionic acid derivative, the second β-aminopropionic acid derivative and unconverted secondary amine;
   (iii) removing the unconverted secondary amine by distillation, and/or
   (iv) removing the second β-aminopropionic acid derivative by distillation;
   wherein 0.9 to 1.10 mole of the acrylic acid derivative is used per mole of the primary amino groups of the amine of value.

2. The process according to claim 1, wherein the acrylic acid derivative is used in stoichiometric excess with regard to the primary amino groups of the primary amine.

3. The process according to claim 1, wherein the acrylic acid derivative is used in an essentially equimolar amount or in stoichiometric deficiency with regard to the primary amino groups of the primary amine.

4. The process according to claim 1, wherein the acrylic acid derivative is acrylonitrile or an acrylic ester.

5. The process according to claim 1, wherein the secondary amine used in step (ii) is a low-boiling amine with a boiling point up to 100° C. and step (iii) is carried out.

6. The process according to claim 1, wherein the secondary amine used in step (ii) is a di($C_1$-$C_4$-alkyl)amine.

7. The process according to claim 1, wherein the secondary amine used in step (ii) is dimethylamine.

8. The process according to claim 1, wherein step (i) is carried out in the presence of water as a catalyst at a temperature of from 20 to 80° C.

9. The process according to claim 1, wherein each amine functionality of the primary amine is substituted only once by an acrylonitrile residue.

10. The process according to claim 4, wherein the acrylic ester is methyl acrylate or ethyl acrylate.

11. The process according to claim 1, wherein a molar ratio of the secondary amine to the unconverted acrylic acid derivative is 1.5:1 to 10:1.

12. The process according to claim 1, wherein the primary amine is isophoronediamine.

* * * * *